United States Patent [19]
Severson

[11] 3,943,915
[45] Mar. 16, 1976

[54] INTRACRANIAL PRESSURE SENSING DEVICE

[75] Inventor: Gerald R. Severson, Scottsdale, Ariz.

[73] Assignee: Motorola, Inc., Chicago, Ill.

[22] Filed: Nov. 29, 1974

[21] Appl. No.: 528,118

[52] U.S. Cl. .................. 128/2 P; 73/398 C; 73/406
[51] Int. Cl.² ........................................... A61B 5/07
[58] Field of Search ........ 128/2 R, 2 P, 2 S, 2.05 D, 128/2.05 E, 2.05 P; 73/398 C, 406, 431, DIG. 6

[56] References Cited
UNITED STATES PATENTS

| | | | |
|---|---|---|---|
| 3,034,356 | 5/1962 | Bieganski et al. | 128/2 P |
| 3,040,736 | 6/1962 | Jackson | 128/2.05 P |
| 3,243,496 | 3/1966 | Silverstein | 73/431 |
| 3,757,770 | 9/1973 | Brayshaw et al. | 128/2.05 D |

*Primary Examiner*—William E. Kamm
*Attorney, Agent, or Firm*—Harry M. Weiss; Kenneth R. Stevens

[57] ABSTRACT

A fluid pressure sensor for use internal to the human body including a completely ceramic sectioned outer shell having an opening therein for allowing fluid access to a thin metal diaphragm member. The thin metal diaphragm member is disposed between the sectioned outer shell by diffusion bonding in order to limit exposure of the human tissue solely to the diaphragm member and the ceramic shell. A variable tuned LC circuit is responsive to fluid pressure for establishing a predetermined electrical parameter. The electrical parameter is capable of affecting an electromagnetically responsive electrical circuit means located external to the human body for providing data indicative of the fluid pressure. The thin diaphragm member constitutes one plate of the LC circuit and the remainder of the LC circuit is located beneath the thin diaphragm member so as to be protected from fluid and moisture.

9 Claims, 2 Drawing Figures

3,943,915

INTRACRANIAL PRESSURE SENSING DEVICE

BACKGROUND OF THE INVENTION

1. Field of Invention

This invention relates to a fluid pressure sensor, and more particularly to a pressure sensor which can be used internal to the human body.

2. Description of Prior Art

Often intracranial pressure measurements and evaluations must be made at regular intervals over a long period of time, and in many instances for years. One measurement technique is the employment of a special type of needle which is inserted into the cranium. This approach is not only unpleasant but also introduces the danger of bacteria and hemorrhaging.

Other implantable pressure sensing devices have been suggested, but many of these prior art devices require contacts or probes to be connected to the sensing device during pressure measurements. Improvements over the contact or probe type of sensors suggest the implantation of an intracranial pressure sensing device devoid of probes or contacts during sensing. One known device employs a battery operated pressure related transmitting implanted device whose signal is sensed by telemetry techniques. However, this device has a relatively short lifetime since it requires batteries and moreover is size limited as it requires a mechanical switch.

Careful consideration also must be given to materials used to form the sensor housing in order to minimize tissue reactivity. The material must be safe to the human patient and also impervious to moisture. Entry of moisture or liquid into the electrical portions of the sensor deleteriously affect its operation.

SUMMARY OF THE INVENTION

It is therefore an object of the present invention to provide an intracranial sensor for measuring fluid pressures which does not require direct connections to the outside world.

Another object of the present invention is to provide an intracranial pressure sensor which is safe to the human body and possesses a long lifetime.

A further object of the present invention is to provide an intracranial pressure sensor of a practical size which is safe to the human body and yet impervious to moisture so as to insure accurate functioning of the electrical portion of the device.

Another object of the present invention is to provide an intracranial pressure sensor device which exposes only a safe two-material system to human tissues.

A further object of the present invention is to provide an intracranial pressure sensor having a flexible diaphragm portion which is highly sensitive to pressure variations without allowing moisture or liquid to enter the electrical parameter portion of the device.

In accordance with the aforementioned objects, the present invention provides upper and lower ceramic shell members having a thin metal diaphragm secured at a peripheral shoulder portion disposed between the upper and lower members by a metallized diffusion bond. In response to fluid pressure, the metal diaphragm functions as part of the variable capacitor which interacts with attendant electrical impedance means located below the metal diaphragm for establishing a predetermined electrical parameter. The electrical parameter is capable of effecting electromagnetically responsive circuit means located external to the body for providing data indicative of fluid pressure. Only the ceramic members and a safe metal diaphragm member are exposed to human tissue.

DESCRIPTION OF THE PREFERRED EMBODIMENTS

Figure 1:
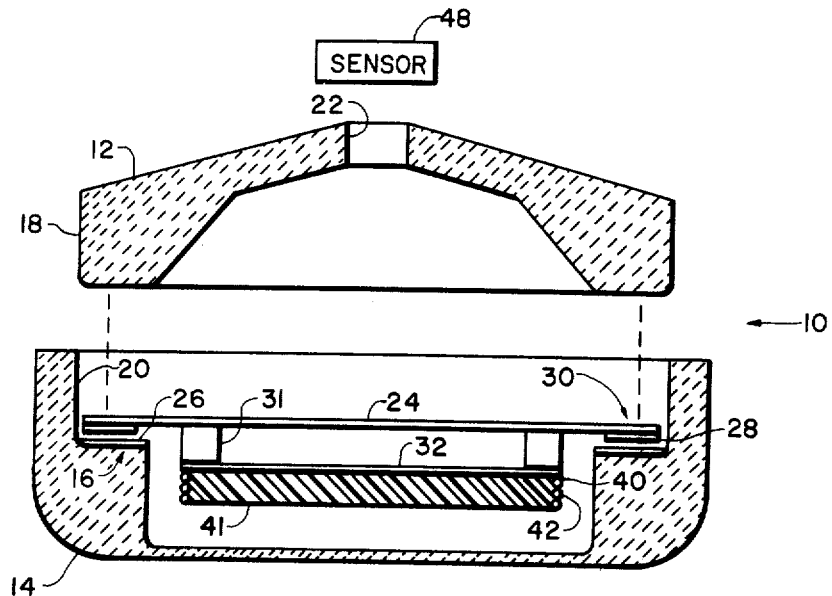
FIG. 1 is a partially exploded cross-sectional view illustrating the upper and lower ceramic housing members and the pressure responsive variable electrical elements capable of establishing a predetermined electrical parameter.

Now referring to FIG. 1, it illustrates a housing 10 comprising an upper and lower shell 12 and 14, respectively. The lower shell 14 includes a peripheral shoulder 16 which extends inwardly. The upper shell 12 contains a peripheral sidewall 18 which is adapted for engagement with an inner sidewall 20 associated with the lower shell 14. In this preferred embodiment both upper and lower shells 12 and 14 are formed from a high quality alumina material constituted by approximately 99.5 percent $Al_2O_3$ and which, for example, is commercially available from the Coors Corporation. The ceramic upper shell 12 contains a centrally disposed opening 22 which allows fluid entry when the device is implanted in a human body.

A thin stainless steel metal diaphragm member 24 is bonded to the peripheral shoulder 16 by means of a gold diffusion bond. In the preferred embodiment the thin diaphragm member 24 is constituted by a 0.001 inch stainless steel medical grade metal member. In order to bond the thin diaphragm member 24 to the peripheral shoulder 16, a thin layer of gold 26 is deposited on the shoulder 16. Also, a thin layer of gold 28 is deposited at the peripheral undersurface of the thin diaphragm 24 as shown at 28. Pressure is then applied to the upper surface of the diaphragm 24 in the area indicated by arrow 30 in order to effect a diffusion bond between the gold layers 26 and 28. It was found necessary to employ an annealed metal diaphragm member 24 in order to prevent fracturing of the diaphragm member during application of the pressure for effecting the diffusion bond.

Figure 2:
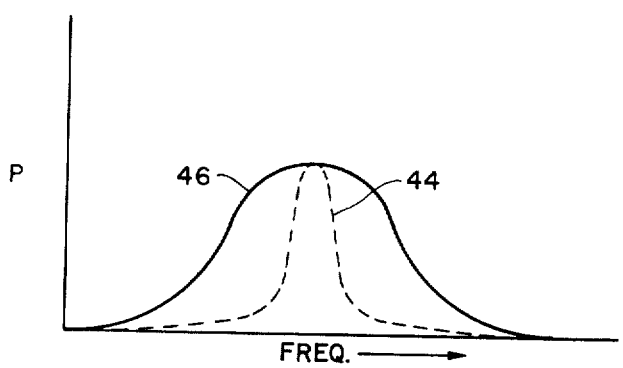
FIG. 2 is a plot showing the high Q circuit response attainable with a structure of FIG. 1.

An insulator spacer 31 is secured to the undersurface of the diaphragm member 24. In addition to being pressure responsive, the diaphragm member 24 constitutes one plate of a variable capacitor. The other plate of the capacitor is constituted by a 0.005 inch stainless steel 302 medical grade member 32 secured to the insulator spacer 31. In the preferred embodiments, the spacer 31 is constituted by a 0.005 inch thick polyimide material which is secured to the undersurface of member 24 and to the upper surface of member 32 by means of a suitable insulative adhesive, such as an epoxy film adhesive. An inductor is constituted by an epoxy coil form 0.085 inches thick and 0.010 diameter gold wires 41 and 42, respectively. The inductor is secured to member 32 by means of a suitable adhesive. A thin gold layer 40 extends across the entire length of the coil line and aids in obtaining the high Q resonant response illustrated in FIG. 2. Curve 44 represents the improved response obtained over curve 46 measured without the layer 40. The thin gold layer is achieved by inserting a 36 gauge gold preform between member 32 and the coil form 41 during assembly.

In order to form the unitary housing 10, the lower surfaces 18 and 20 are first ground and lapped and then the upper shell 18 is cooled to approximately −40°F. and the lower shell 14 is heated to approximately 150°F. This allows the top shell to be inserted within the lower shell and when the structure returns to ambient conditions, relative expansion and contraction of the upper and lower members insures an extremely tight fit between surfaces 18 and 20 for locking them together to form a unitary shell or housing.

In operation, the parallel tuned LC circuit formed by the variable conductor and inductor constitutes a high Q resonant circuit whose frequency varies as a function of spacing between the capacitor plates 24 and 32. The capacitor value varies as a result of fluid pressure being exerted via opening 22 on the upper surface of diaphragm or capacitor plate member 24. Prior to sealing the upper and lower shells 12 and 14 with the pressure joint, the tuned circuit is empirically calibrated to relate pressures to a plurality of associated peak resonant frequencies. Thus, an electromagnetically responsive sensor means 48 can be located external and in close proximity to the human body, such as a grid-dip transducer, and is effective to vary the frequency of an inductively coupled oscillator detector in order to provide an indication of the pressure being exerted on the diaphragm member 24. It can be seen that the entire device is fabricated from materials safe to the human body and thus, even in the event of a catastrophic failure such as a break in the seal between surfaces 18 and 20 or a rupture in the diaphragm member 24, the human body is not exposed to dangerous materials.

While the invention has been particularly shown and described in reference to the preferred embodiments thereof, it will be understood by those skilled in the art that changes in form and details may be made therein without departing from the spirit and scope of the invention.

What is claimed is:

1. A body fluid pressure sensor for use internal to a human body, particularly intracranial, comprising:
   a. a ceramic housing having an upper and lower member;
   b. said lower member having an internal cavity recessed portion located within said ceramic housing and a peripheral shoulder portion extending inwardly from the upper portion of said internal cavity recessed portion and said upper member having an opening for body fluid;
   c. a thin metal diaphragm member affixed at its outer edges to said peripheral shoulder portion;
   d. a metallized diffusion bond for attaching said thin metal diaphragm member to said peripheral shoulder portion for hermetically sealing said internal cavity recessed portion;
   e. an electrical impedance means located within said internal cavity recessed portion, said thin metal diaphragm member constituting a portion of said electrical impedance means and being responsive to fluid pressure on said thin metal diaphragm member for establishing a predetermined electrical parameter; and whereby
   f. sensor means located external to the human body is responsive to said predetermined electrical parameter for providing data indicative of said fluid pressure.

2. A fluid pressure sensor as in claim 1 wherein:
   a. said electrical impedance means further comprises a metal plate insulatively spaced from said thin metal diaphragm member for constituting a capacitor and an inductor coupled to said capacitor for electromagnetically coupling to said sensor means located external to the human body for providing data indicative of said predetermined body fluid pressure being exerted on said thin metal diaphragm member.

3. A fluid pressure sensor as in claim 2 wherein:
   a. said upper member is secured to said lower member by an expansion joint.

4. A fluid pressure sensor as in claim 3 wherein:
   a. said metallized diffusion bond comprises a gold bond.

5. A fluid pressure sensor as in claim 4 wherein:
   a. said diaphragm member extends entirely across said internal cavity recessed portion so as to expose the human body only to said ceramic housing and said metal diaphragm member.

6. A fluid pressure sensor as in claim 5 wherein:
   a. said thin metal diaphragm member is annealed stainless steel.

7. A fluid pressure sensor as in claim 6 wherein:
   a. said ceramic housing comprises a high grade alumina material.

8. A fluid pressure sensor as in claim 7 wherein:
   a. said sensor means includes an inductively coupled frequency responsive oscillator means for measuring said electrical parameter.

9. A body fluid pressure sensor for use internal to a human body, particularly intracranial, comprising:
   a. a ceramic housing including an upper and lower member;
   b. said upper member having an opening for allowing body fluid ingress, said lower member having an internal cavity;
   c. a thin metal diaphragm member affixed at its outer edges to said lower member;
   d. a metallized diffusion bond disposed between the thin metal diaphragm member outer edges and said lower member for hermetically sealing said internal cavity;
   e. an electrical impedance means located within said internal cavity and coupled to said thin metal diaphragm member, said thin metal diaphragm member constituting a portion of said electrical impedance means and being responsive to body fluid pressure on said thin metal diaphragm member for establishing a predetermined electrical parameter; and whereby
   f. sensor means located external to the human body is responsive to said predetermined electrical parameter for providing data indicative of said body fluid pressure.

* * * * *